(12) United States Patent
Berger

(10) Patent No.: US 8,216,185 B2
(45) Date of Patent: Jul. 10, 2012

(54) CANNULATED APERTURED GROOVED DIRECTOR

(76) Inventor: J. Lee Berger, Franklin Lakes, NJ (US)

(*) Notice: Subject to any disclaimer, the term of this patent is extended or adjusted under 35 U.S.C. 154(b) by 267 days.

(21) Appl. No.: 12/289,076

(22) Filed: Oct. 20, 2008

(65) Prior Publication Data

US 2010/0100046 A1 Apr. 22, 2010

(51) Int. Cl.
*A61M 5/178* (2006.01)
*A61M 25/00* (2006.01)

(52) U.S. Cl. .................. 604/164.01; 604/264

(58) Field of Classification Search .......... 604/114–116, 604/137, 128, 131, 138, 264, 164.01–170.01; 600/114–116, 128, 131, 138, 137
See application file for complete search history.

(56) References Cited

U.S. PATENT DOCUMENTS

| 2,164,926 | A | | 7/1939 | Kleine |
| 3,537,452 | A | | 11/1970 | Wilks |
| 3,559,643 | A | | 2/1971 | Pannier, Jr. et al. |
| 3,592,193 | A | | 7/1971 | Higgins |
| 4,645,491 | A | | 2/1987 | Evans |
| 4,655,214 | A | | 4/1987 | Linder |
| 4,863,439 | A | * | 9/1989 | Sanderson ............. 604/264 |
| 4,905,667 | A | * | 3/1990 | Foerster et al. ........ 600/104 |
| 5,011,478 | A | | 4/1991 | Cope |
| 5,545,136 | A | | 8/1996 | Berger |
| 6,706,069 | B2 | | 3/2004 | Berger |
| 2008/0065020 | A1 | * | 3/2008 | Ralph et al. .......... 604/164.11 |

* cited by examiner

*Primary Examiner* — Jackie Ho
*Assistant Examiner* — Leah Stohr
(74) *Attorney, Agent, or Firm* — John S. Hale; Gipple & Hale

(57) ABSTRACT

A surgical instrument including a fixed or removable handle and a tubular member having a lumen extending therethrough with apertures at its proximal and distal ends permitting visualization of and access to body tissues. An access window in a distal portion of the instrument is formed through the wall of the tubular member and in communication with the lumen.

10 Claims, 3 Drawing Sheets

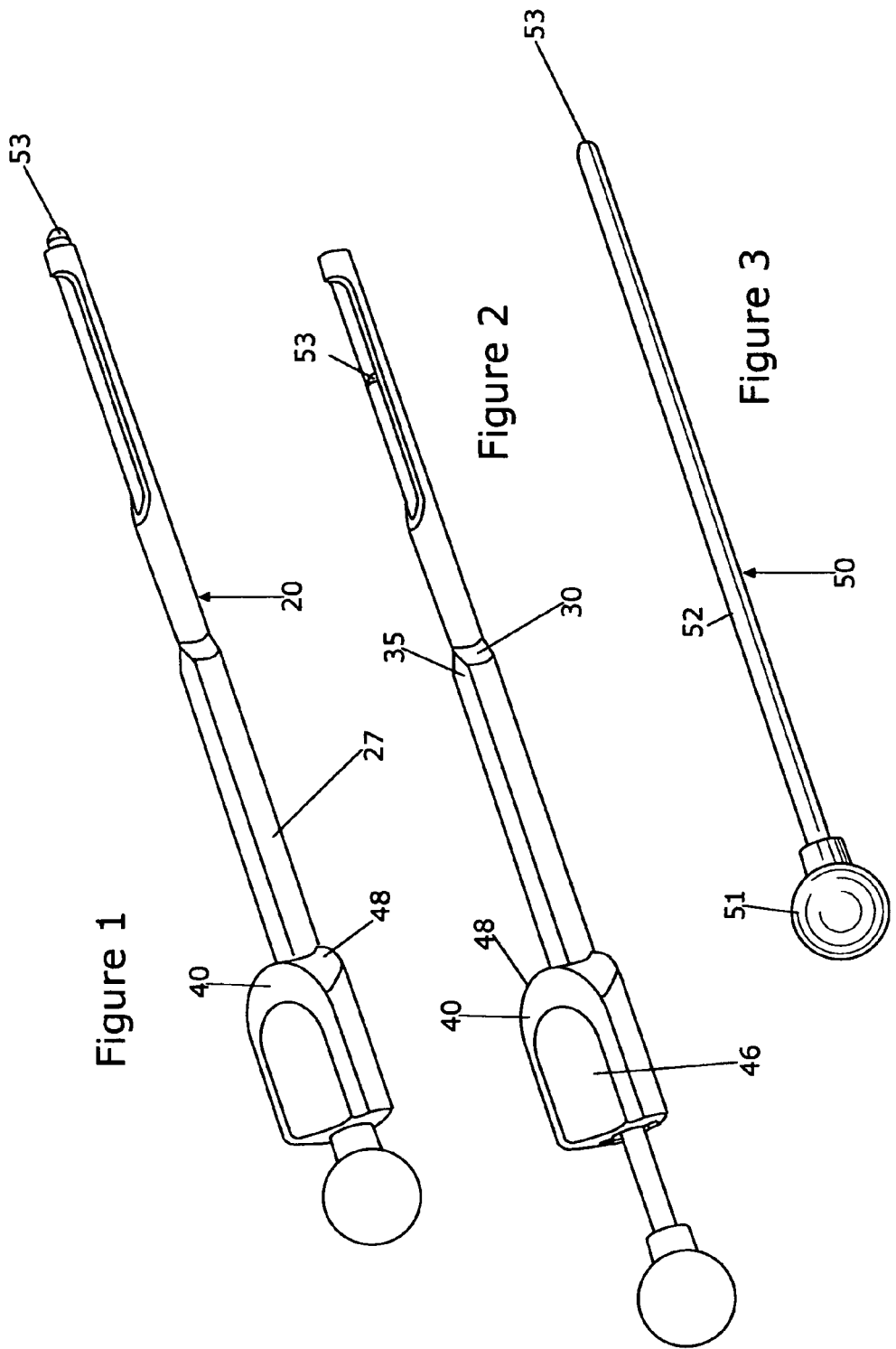

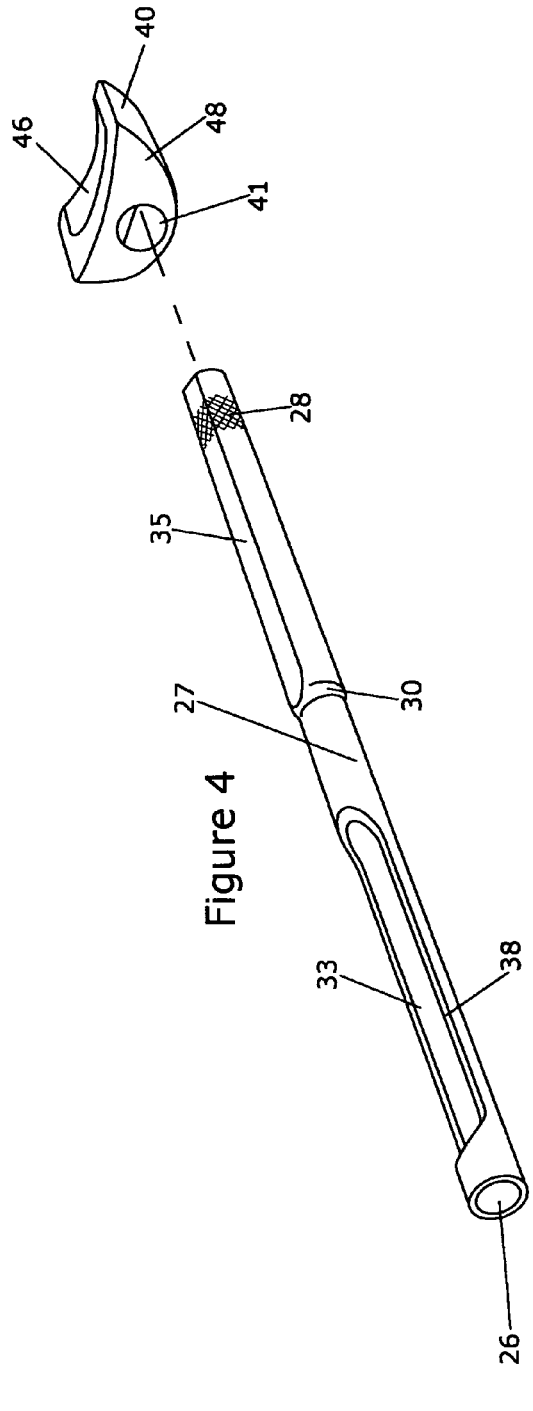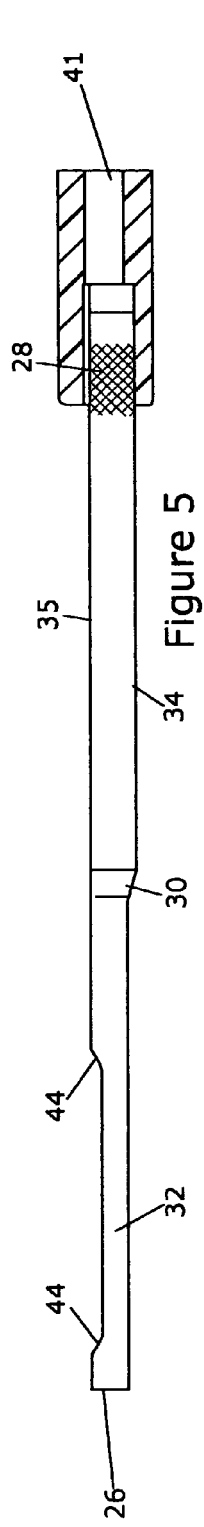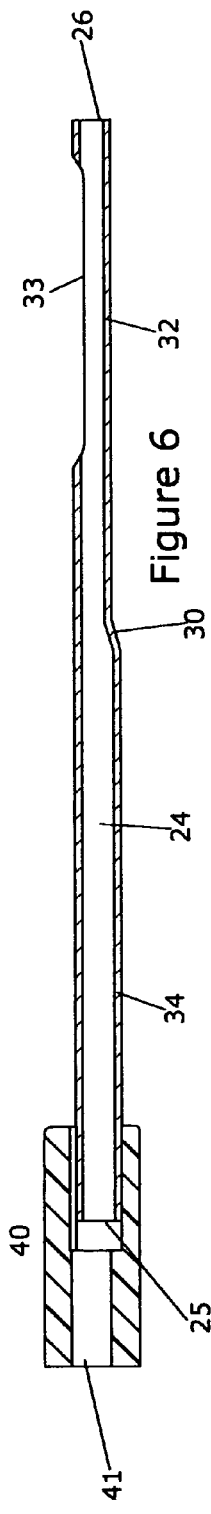

CANNULATED APERTURED GROOVED DIRECTOR

RELATED APPLICATIONS

None

STATEMENT REGARDING FEDERALLY SPONSORED RESEARCH OR DEVELOPMENT

None

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention relates to a cannulated tubular instrument for access and visualization of body tissues. The apparatus aids insertion of catheters and other instruments into the body of a patient and can be used in combination with a trochar inserted into its lumen to bluntly dissect obstructing tissues before placement of the implement. Additionally, the instrument includes multiple apertures on its distal portion to facilitate visual and physical access to target body tissues.

2. Background of the Invention

The use of a cannula, sheath, or director to guide or ease insertion of surgical instruments or to facilitate access to a surgical field is well known. In addition, a rigid trochar or trochar-like assembly is often included that can be inserted into the cannula to bluntly dissect tissues during insertion of the device.

For example, U.S. Pat. No. 5,545,136 issued Aug. 13, 1996, a patent issued to the present inventor, discloses a surgical instrument used in the treatment of carpal tunnel syndrome having a rigid tubular member with lumen through which a balloon carpal tunnel plasty procedure may be undertaken. The balloon expands through an aperture in the radial wall of the tubular member and the tubular member includes a rigid, solid rounded tip to ease insertion of the apparatus into the carpal tunnel. Other instruments are then used in conjunction with the instrument to perform the surgery. U.S. Pat. No. 6,706,069 issued Mar. 16, 2004, also to the present inventor, is directed toward a grooved director with a built in balloon which is inflated by a pump to a predetermined pressure to expand the walls of a collapsed vertebra. The device is inserted into the body of the compressed vertebra and the grooved director is positioned and aimed in a direction under the compressed superior end plate of the vertebral body. The balloon inside of the grooved director is inflated and the force and direction of balloon inflation restores the height of the fractured vertebrae. The balloon is deflated and the grooved director is circumferentially rotated while intermittently inflating and deflating the balloon to create a symmetrical space within the center of the vertebral body. The balloon is deflated and the grooved director device with balloon is removed leaving a rebuilt vertebra which may be filled with a biocompatible material. U.S. Pat. No. 4,655,214 issued Apr. 7, 1987 shows a soft inflatable sheath having a closed rounded distal tip that is inserted through a catheter and inflated adjacent the distal tip of the catheter prior to intubation. The proximal end of the sheath is sealed to maintain it in an expanded condition when the catheter is being intubated. Following intubation the cylindrical sheath is deflated and withdrawn U.S. Pat. No. 4,645,491 issued Feb. 24, 1987 shows a catheter placement apparatus used in inserting a catheter to a preferred depth. The device comprises a surgical needle provided with a thin-walled transparent polytetrafluoroethylene tube which is heat shrunk over the stem portion of the needle to form a longitudinal window allowing a catheter inserted in the needle to be viewed. The catheter has a colored patch of the same length as the window and a series of spaced circular bands of differing colors allowing the position of the catheter to be accurately located by lining the colored patch with the window and advancing the catheter until at least one band appears in the window. The color and distance of the band nearest to the surface of the patient's skin are used to determine the position of the catheter. The surgical needle is withdrawn by sliding it along and off the catheter. U.S. Pat. No. 2,164,926 issued Jul. 4, 1939 shows a catheter stylet with an eye or aperture positioned on an opposite lateral wall behind the tip. U.S. Pat. No. 3,537,452 issued Nov. 3, 1970 shows a needle guard and beveled cutter for use with intravenous catheterization units. The device has a tubular body with a flat base and a longitudinally slotted top. The diameter of the tube is greater than the diameter of the needle contained therein. U.S. Pat. No. 3,592,193 issued Jul. 13, 1971 shows a removable needle guide used with a flexible catheter tube in withdrawing or introducing fluids relative to a body. The hollow tubular needle guide has a sharpened needle portion provided at its proximal end for puncturing the skin, tissues and veins of the body where the needle is inserted. At its distal end, the guide has winged handles which provide controlled insertion and removal from the body with subsequent attachment from a flexible catheter tube. U.S. Pat. No. 5,011,478 issued Apr. 30, 1991 shows an introducer set including a sheath and dilator formed with a smooth external shape. The distal end of the sheath is embedded in the dilator and formed in angle oblique to the longitudinal access of the introducer set. U.S. Pat. No. 3,559,643 issued Feb. 2, 1971 shows a catheter placement unit for insertion of a catheter into a body lumen through an incised opening in the lumen wall. The unit includes a longitudinally slit sheath having a catheter therein and an advancer connected to one end of the catheter, initially in axial alignment with the sheath to close the end of the sheath.

There is presently a need, however, for an orthopedic and general surgical manual instrument that combines various features of these multiple instruments. Such an instrument is usable as a combination director, probe, cannula, elevator, flexible arthroscope/endoscope laser guide, and cutting guide for orthopedic and general surgery. Now a common component of many surgical procedures, arthroscopes and endoscopes utilize fiber optic technology to allow the surgeon to visualize interior tissues through a small incision. Rigid arthroscopes and endoscopes have visual fields limited by the angle of their lens. Conversely, flexible arthroscopes/endoscopes enable the surgeon to visualize multiple angle locations during surgery but the flexibility which makes them more useful in visualizing the surgical site also makes them difficult to position due to the resistance of the tissues being examined. Inserting the flexible arthroscope/endoscope into a cannula of the present invention facilitates positioning in the body and provides protection for the device.

SUMMARY OF THE INVENTION

The present invention is a multi-functional, cannulated, apertured, grooved director and insertional trochar. It includes a generally rigid, stepped tubular member having a throughgoing bore extending through the device through which additional surgical instruments may be inserted. An aperture forming an access window is positioned adjacent the distal end of the device and commensurate with the throughgoing bore so that instruments can be passed through or inserted into the director. These instruments include mechanical or balloon catheter devices, surgical probes, surgical blades of various sizes and dimensions, surgical lasers, electrocautery devices, and ultrasound, electrical, magnetic, radiofrequency, and/or biological devices.

The present invention is ideally suited for hand and wrist surgery, particularly with regard to endoscopic, balloon assisted carpal tunnel release or wrist arthroscopy. Additional open and arthroscopic surgical uses will be immediately obvious to those skilled in the art and include use in a variety of elbow, shoulder, hip, knee, ankle, and foot procedures.

The device is particularly useful as a working cannula that allows the surgeon to direct a flexible scope in multiple directions within its confines. The access window of the present invention enables the surgeon to direct the arthroscope/endoscope therethrough. Where the arthroscope/endoscope includes a laser or is used in conjunction with a laser, the device enables the surgeon to visualize structures and operate the laser tip at multiple angles.

The device is also useful as a cutting guide to protect surrounding tissues from inadvertent laceration by the surgeon. The director is positioned such that its access window is directly beneath the tissue needing to be cut. The access window may then be used to guide a scalpel or similar cutting implement, while surrounding tissues are protected by the device body defining the aforementioned window.

It is an object of this invention to provide a multi-functional surgical instrument.

It is another object of this invention to provide a combination director, probe, cannula, elevator, and cutting guide for orthopedic and general surgery.

It is still another object of this invention to provide a multi-functional surgical instrument in multiple sizes to accommodate various surgical procedures and instrumentation.

It is an object of this invention to provide an inexpensive to manufacture, biologically inert, and autoclavable surgical instrument.

It is yet another object of this invention to facilitate use of flexible arthroscopes and endoscopes.

It is an object of this invention to provide a surgical laser guide.

It is another object of this invention to provide a surgical cutting guide.

It is yet another object of this invention to provide a director for surgical instruments.

It is an object of this invention to provide a surgical probe.

It is an object of this invention to provide a surgical elevator.

It is another object of this invention to provide a cannula for surgical instruments.

BRIEF DESCRIPTION OF THE DRAWINGS

FIG. 1 is a perspective view of the multi-functional, cannulated, apertured, grooved director with a trochar inserted;

FIG. 2 is a perspective view of the director in FIG. 1 with the trochar partially withdrawn;

FIG. 3 is a perspective view of the trochar partially depicted in FIGS. 1 and 2;

FIG. 4 is a perspective view of a preferred embodiment of the grooved director with handle removed;

FIG. 5 is a side elevation view of the invention rendered in FIG. 4 with its removable handle depicted in cross section;

FIG. 6 is cross sectional view of the invention rendered in FIG. 4 taken from a reversed view of FIG. 5;

Figure 7:
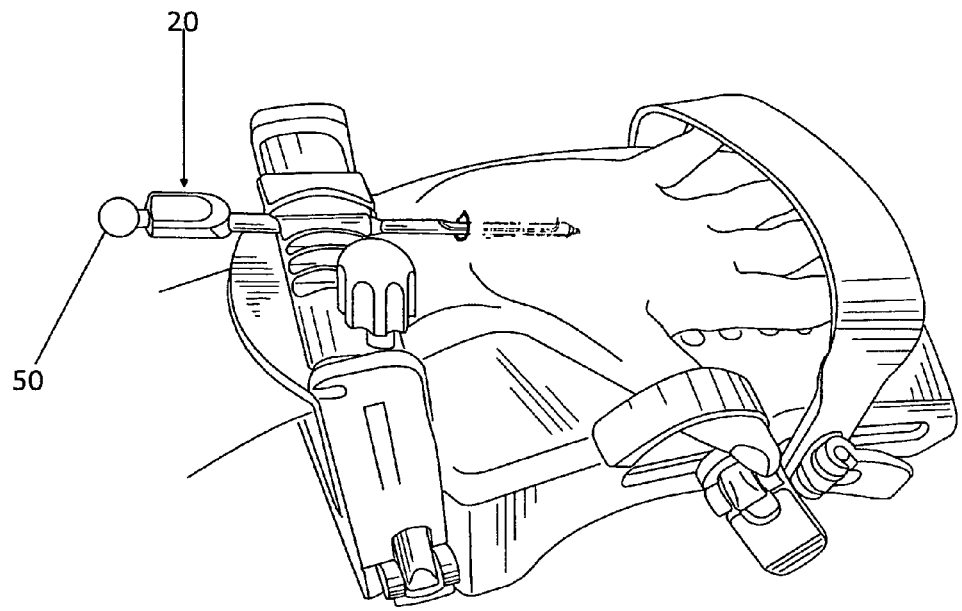
FIG. 7 is a perspective view of the invention in use during a surgical procedure; and, FIG. 8 is a perspective view of the invention with a flexible endoscope inserted.

These and other objects, advantages, and novel features of the present invention will become apparent when considered with the teachings contained in the detailed disclosure along with the accompanying drawings.

DESCRIPTION OF THE INVENTION

While the invention is described in connection with certain preferred embodiments, it is not intended that the present invention be so limited. On the contrary, it is intended to cover all alternatives, modifications, and equivalent arrangements as may be included within the spirit and scope of the invention as defined by the appended claims.

The invention is a cannulated, stepped and generally tubular instrument open at both its proximal and distal ends. An access window is formed adjacent the distal end of the device with the base of the access window being an open curved channel. The curved channel is axially aligned with a throughgoing bore which runs through the proximal tubular section of the instrument. A flattened, ergonomically shaped handle with a throughgoing bore is mounted at the proximal end over the tube distal end to facilitate precise control of the device while in use. The handle is semi-circular in cross section with a flat top defining a finger recess. About one-half of one inch of the surface of the proximal end of the generally tubular portion of the device is knurled, thereby ensuring precise control is maintained whether the handle is used or detached. A needle-like trochar may be provided, sized to closely fit the interior diameter of the device and of a length such that, when inserted into the lumen of the present invention, its distal tip slight protrudes from the distal aperture of the instrument. In use, the trochar is inserted into the multi-functional, cannulated, apertured, grooved director of the present invention so that its blunted tip may be used to dissect away tissue to facilitate placement of the device without injury to the surrounding tissues.

The device can be manufactured from stainless steel, cobalt chrome, titanium, nitinol, other metals, polymers, ceramics, composites or other biocompatible materials, and can be manufactured in various sizes and dimensions.

A preferred embodiment and best mode of the invention is shown in FIGS. 1-2, and 4-6. The multi-functional, cannulated, grooved director 20 is constructed from surgical steel or polymer material forming its tubular member 27, with an ergonomically shaped handle 40 mounted at its proximal end. The tubular member 27 is cannulated, having a throughgoing, generally cylindrical lumen 24 extending throughout the length of the proximal section and on both ends of the distal section, with proximal 25 and distal 26 apertures in communication with the lumen 24. Member 27 is stepped at 30 to provide a thinner diameter distal tube section 32 while providing strength near its handle 40 via proximal tube section 34. The proximal tube section 34 of the tubular member 27 proximal to step 30 defines a planar top surface 35 extending the length of the proximal section and functions to securely fix the handle 40 about the tubular member 27 and provide anti-roll characteristics to the member 27. The tubular member 27 is cut so that a portion of its wall removed adjacent its distal end to form an access window 33 having beveled ends 44, thereby exposing the lumen 24 of the device. In the most preferred embodiment, the access window 33 is defined by radiused proximal and distal ends 44 and generally parallel side ends 38 of the cutaway tubular section 32.

The handle 40 of the device is formed from a polymer material and is ergonomically shaped to facilitate handling of the instrument 20. In a preferred embodiment, the handle 40 is generally planar on its top surface 42 and defines a recessed concave surface 46 which accommodates the surgeon's thumb to ensure positive control of the grasped device. As seen most clearly in FIG. 4, a throughgoing lumen 41 extends through the handle and is axially aligned with and in communication with the proximal aperture 25 of the tubular member 27. The handle 40 has a semi-circular cross section and a round convex front surface 48. In one embodiment, the handle 40 is permanently affixed to the tubular member 27 via an adhesive or sonic welding. If desired both the handle and tube can be formed from a single piece of material such as stainless steel or rigid medically approved plastic material, for example polyethylene or polypropylene. As depicted in FIG. 4, the handle 40 is frictionally mounted to the tubular member 27 and may be detached as desired. The planar portion 35 of the tubular element 27 results in an eccentrically shaped cross section such that the corresponding handle lumen 41 ensures positive engagement of the handle 40 to the proximal end of the tubular element. The cross sections of the proximal end of the tubular element 27 and the handle lumen 41 ensure that when mated, the handle 40 and tubular element 27 are fixed and cannot rotate relative to one another. The proximal portion of the tubular element 27 includes knurling 28, as shown in FIGS. 4 and 5, to ensure positive handling of the tubular element 27 when the handle is not attached and to increase friction and positive attachment of the handle 40. When handle 40 is not attached, the planar portion 35 of the tubular element 27 minimizes the opportunity for the tubular element 27 to roll off the work surface.

As depicted in FIG. 3 (and partially in FIGS. 1 and 2), a trochar 50 is included for blunt dissection of tissues during placement of the director 20. The trochar 50 comprises a handle 51 mounted to the proximal end of an elongated cylindrical solid trochar body 52 sized to closely fit the lumen 24 of the director 20. The distal end of the trochar 50 forms a rounded blunt tip 53 such that when the trochar 50 is inserted into the director 20, the blunt tip 53 protrudes slightly from the distal aperture 26 of the tubular member 27, as seen in FIG. 1. The trochar 50 can be manufactured from stainless steel, cobalt chrome or other alloys, titanium, nitinol as well as plastic or ceramic.

Exemplary operation and use of the director 20 and trochar 50 are depicted in FIG. 7 with regard to surgery on the hand. Also depicted is a surgical hand support that is the subject of U.S. Pat. No. 5,881,730, which may be used in conjunction with this invention. An incision is first cut through the skin and subcutaneous tissue by sharp dissection. The trochar 50 may optionally by inserted into the director 20 and this combination utilized to further bluntly dissect the surgical site. Thereafter, the director 20 is used to guide arthroscopy/endoscopy, facilitate fine targeting of lasers and direct the positioning of other surgical tools, and elevate or retract tissues away from the surgical field without damage. The device may also be used for these, and additional functions known to those skilled in the art, with and without additional support.

Figure 8:
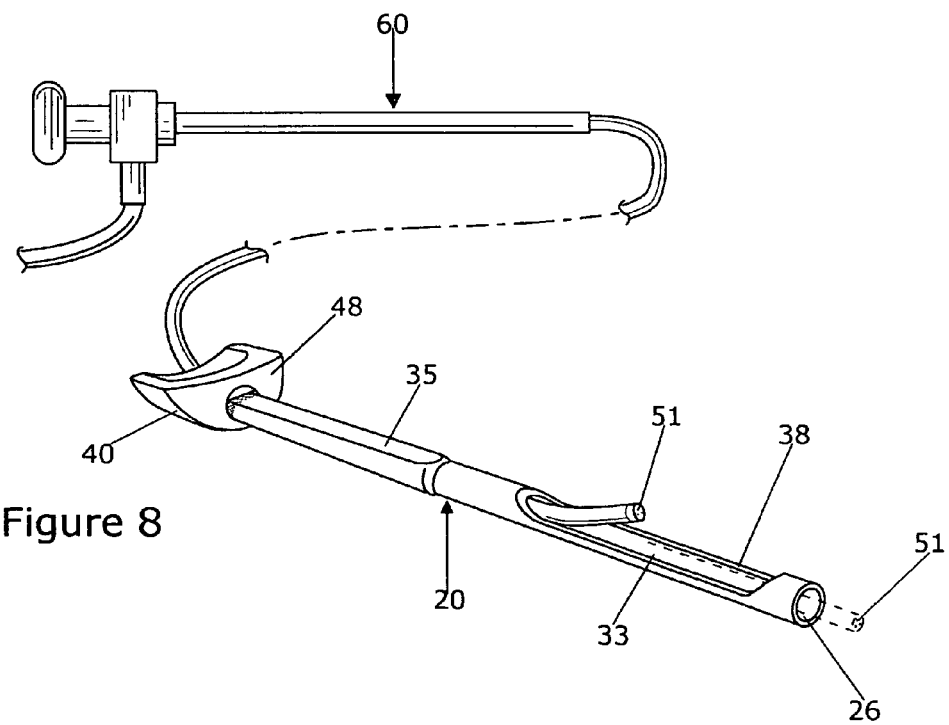

FIG. 8 depicts use of the director 20 of the present invention in combination with a flexible endoscope 60 such as an Olympus Flexible Ureteroscope URF-P3. The tip of the flexible endoscope 61 is shown protruding from the access window 23 as well as from its distal aperture 26. This allows 360 degree visualization of the surgical site and allows the camera and laser portion of the tip of the scope to be directed at multiple angles to enhance visualization during surgical procedures as well as enhance direction and performance of the laser. The present apparatus can be used for open and arthroscopic procedures in hand and wrist surgery, elbow surgery, shoulder surgery, hip surgery, knee surgery, and ankle and foot surgery.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims.

What is claimed is:

1. A surgical tool comprising:
an elongated substantially rigid tubular member with a proximal section defining a planar surface and a stepped distal section, said tubular member defining a lumen extending therethrough and defining apertures at said proximal and distal ends in communication with said lumen, said tubular member defining an access window in said distal section in communication with said lumen, a handle mounted on a proximal end of said tubular member, and a trochar sized to fit said lumen, said trochar having a trochar handle and a linear cylindrical member with a distal blunt tip which protrudes slightly from said distal end of said tubular member when inserted into said tubular member, said handle being a removable handle mounted to said proximal end of said tubular member and being substantially semi-circular in cross section with a planar face and a recess defined in said planar face.

2. A surgical tool as claimed in claim 1 wherein said lumen of said tubular member is sized to accept a surgical tool taken from the group consisting of mechanical catheter devices, balloon catheter devices, surgical probes, surgical blades, surgical lasers, electrocautery devices, ultrasound devices, electrical devices, magnetic devices, radiofrequency devices, and biological devices.

3. A surgical tool as claimed in claim 1 wherein said lumen of said tubular member is sized to accept an arthroscope or endoscope for visualization of body structures.

4. A surgical tool as claimed in claim 1 wherein said tubular member includes a planar surface coincident with and generally parallel to the longitudinal axis of said tubular member.

5. A surgical tool as claimed in claim 1 wherein said access window has a channeled base and beveled ends.

6. A surgical tool as claimed in claim 1 wherein said aperture at said distal end is sized to permit up to about 360 degree visualization of the surgical site via a device selected from a group consisting of an endoscope, endoscope with laser, and arthroscope inserted into the lumen of said surgical tool.

7. A surgical tool as claimed in claim 1 wherein an internal surface of said tubular member adjacent said access window forms a curved groove shaped to accommodate a cutting tool.

8. A surgical tool comprising:
an elongated substantially rigid tubular member defining a longitudinal axis dimensioned to be inserted through tissue, said tubular member having a proximal section with a non-circular cross section and planar outer surface and a distal section with an open elongated access window beveled at each end, said tubular member defining a lumen extending therethrough and defining apertures at said proximal and distal ends in communication with said lumen and said access window and a channel formed at the bottom of said access window, said tubular member having a removable ergonomically shaped handle mounted at said distal end, and a trochar sized to fit said lumen, said trochar having a distal blunt tip which protrudes slightly from said distal end of said tubular member when fully inserted into said tubular member.

9. A surgical tool as claimed in claim 8 wherein said handle defines a central throughgoing bore adapted to fit over the proximal end of said tubular member and defines a planar top surface with at least one finger recess.

10. A surgical tool as claimed in claim 1 wherein said handle is a friction fit on said tubular member proximal section and said tubular member proximal section defines a knurled region.

* * * * *